(12) United States Patent
Tu et al.

(10) Patent No.: US 6,290,697 B1
(45) Date of Patent: Sep. 18, 2001

(54) SELF-GUIDING CATHETER SYSTEM FOR TISSUE ABLATION

(75) Inventors: Hosheng Tu, Tustin; Weng-Kwen Raymond Chia, Irvine; Cary Hata, Tustin, all of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/203,125

(22) Filed: Dec. 1, 1998

(51) Int. Cl.[7] .................................................. A61B 18/04

(52) U.S. Cl. ............................. 606/27; 606/31; 607/101; 607/102

(58) Field of Search .................................. 606/27–29, 31, 606/41, 45–50; 607/96, 98–102, 122

(56) References Cited

U.S. PATENT DOCUMENTS

| 5,103,804 | * | 4/1992 | Abele et al. . | |
| 5,540,679 | * | 7/1996 | Fram et al. | 606/27 |
| 5,562,720 | * | 10/1996 | Stern et al. | 607/98 |
| 5,860,974 | * | 1/1999 | Abele | 606/41 |
| 5,938,660 | * | 8/1999 | Swartz et al. | 606/45 |
| 5,971,983 | * | 10/1999 | Leah | 606/41 |
| 6,012,457 | * | 1/2000 | Lesh | 128/898 |

\* cited by examiner

Primary Examiner—Roy Gibson (57) ABSTRACT

An improved guiding catheter system having inflated balloon at its tip section, wherein the inflated balloon having a plurality of electrodes is heated to a predetermined temperature as an ablation means for delivering the thermal energy to a tissue by deploying the balloon to contact the tissue to cause a circular ablation lesion, the plurality of electrodes using RE energy as a heat source for paroxysmal atrial fibrillation indications.

10 Claims, 5 Drawing Sheets

SELF-GUIDING CATHETER SYSTEM FOR TISSUE ABLATION

CROSS-REFERENCE TO RELATED APPLICATION

This application is related to patent application Ser. No. 08/735,199, filed Oct. 21, 1996, entitled "Cardiovascular Catheter System with an Inflatable Soft Tip", now U.S. Pat. No. 5,891,027, and is incorporated herein by reference.

FIELD OF THE INVENTION

The present invention generally relates to improved constructions for a guiding catheter. More particularly, this invention relates to a guiding catheter containing an inflatable balloon and a guidewire attachment at its tip section for self-guiding to the tissue site for ablation.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardia that are frequently caused by the presence of an "arrhythmogenic region" or "accessory atrioventricular pathway" close to the inner surface of the heart chambers. The heart includes a number of normal pathways that are responsible for the propagation of electrical signals from the upper to the lower chambers necessary for performing normal systole and diastole function. The presence of arrhythmogenic region or accessory pathway can bypass or short circuit the normal pathways, potentially resulting in very rapid heart contractions, referred to here as tachycardia.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to an exact site for ablation. Once at the site, it is important for a physician to control the emission of energy to ablate the tissue within a heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic region and/or accessory pathway are determined. After a mapping study, an ablation catheter is usually introduced to the target heart chamber and is manipulated so that the tip electrode lies exactly at the target tissue sites. Radiofrequency energy or other suitable energy is then applied through the tip electrode to the cardiac tissues in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms.

In the paroxysmal AFib, the origin of the arrhythmia may lie near the ostium of the pulmonary vein. A complete circular lesion is required around the ostium to cure the arrhythmia.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area. For paroxysmal AFib indications, a catheter is approached from the atrium to the ostium of a pulmonary vein. The tip section of a catheter is referred to here as the portion of that catheter shaft containing the electrode means which may be deflectable and may be adapted to form a circular or an irregular-shape complete loop lesion. The electrode means is to be positioned against the ostium of the pulmonary vein, whereby the circular electrode means having a firm support, such as an inflated balloon, can be pressed against the tissue for ablation.

Several patents disclose the use of a guiding introducer to guide the ablation catheter into the place. Examples as U.S. Pat. No. 5,840,027 to Swartz et al., U.S. Pat. No. 5,833,673 to Ockuly et al., U.S. Pat. No. 5,814,029 to Hassett, U.S. Pat. No. 5,814,017 to Hassett et al., U.S. Pat. No. 5,800,413 to Swartz et al., and U.S. Pat. No. 5,725,512 to Swartz et al. However, none of the above-referred patents disclose a self-guiding catheter for ablation of tissues. U.S. Pat. No. 5,840,076 discloses a balloon type electrode catheter by using balloon as a medium to create a circular lesion, wherein the balloon is made of a porous material. Said patent discloses a RF circuit by including a patient in the circuit loop, whereby the heat generated by the RF current at the tissue contact site may unexpectedly hurt the patient. The local heat source may make the temperature of the heated balloon non-uniformly around the balloon.

There is an urgent clinical need to have a self-guiding catheter that can provide a uniformly heated balloon for creating a circular lesion. The temperature of the uniformly heated balloon can be controlled by a temperature sensor and a temperature controller without inducing blood coagulation during ablation operations.

SUMMARY OF THE INVENTION

In general, it is an object of the present invention to provide a guiding catheter that is used to self-guide the guiding catheter having ablation capabilities to the tissue site for ablation. The "self-guiding" catheter is defined as the catheter that has a guidewire, a guide-balloon, a soft tip section, or the like at its distal tip section. It is another object of the present invention to provide a uniformly heated balloon as ablation means for creating a circular lesion at the ostium of a pulmonary vein. It is a preferred object of the present invention to have a bipolar electrode immersed in a conductive or semi-conductive fluid medium for generating heat by RF current. It is still another objective to have an ultrasonic transducer in a fluid medium for generating heat to the fluid by ultrasonic wave. This catheter is particularly useful for treating a patient having paroxysmal atrial fibrillation (AFib) indications by providing thermal therapy through the relatively uniformly heated medium.

In one embodiment, a guiding catheter system comprises a catheter sheath having a sheath distal end, a sheath proximal end, and at least one lumen extending between the sheath distal end and the sheath proximal end. The at least one lumen includes an inflation lumen, wherein the inflation lumen has a lumen proximal end and a lumen distal end. A handle is attached to the sheath proximal end, wherein the handle has a cavity. The guiding catheter also comprises an inflatable balloon having a balloon proximal end and a balloon distal end. The inflatable balloon may serve as a guide-balloon or a soft tip section for the guiding catheter. The guide-balloon or an inflatable balloon has at least one radiopaque marker that can be identified externally of the human body. An inflation medium is used to inflate the inflatable balloon. The inflation medium may be selected from the group consisting of electrically conductive or semi-conductive fluids. Alternately, the inflation medium may be selected from the group consisting of electrically conductive or semiconductive gels. In one embodiment, the electrically conductive or semi-conductive gel may contain a plurality of metal particles, wherein the metal particles are adapted for providing electrical conductivity for the electrically conductive or semi-conductive gel. The "semi-conductivity" is defined in this invention, as that of a medium having about the same order of the conductivity or resistivity like a tissue. The resistivity or impedance for a issue is generally in the range of 10 to 250 ohms, preferably in the range of 25 to 200 ohms.

In another embodiment, the guiding catheter further comprises a sheath tip section that is located close to the sheath distal end. The sheath tip section has a proximal end and a distal end, wherein the lumen distal end of the inflation lumen opens into and is in communication with an interior of the inflatable balloon and wherein the balloon proximal end and/or the balloon distal end of the inflatable balloon are sealed to the catheter sheath at the sheath tip section. When the balloon is secured to the sheath distal end, only the balloon proximal end is sealed to the catheter sheath.

In a preferred embodiment, a plurality of electrodes is mounted close to the lumen distal end of the inflation lumen, each electrode having a conducting wire. The system comprises a RF current generator, wherein the RF current generator is adapted for delivering a RF current to a first electrode of the plurality of electrodes, wherein the first electrode of the plurality of electrodes is adapted for transmitting the RF current to a second electrode of the plurality of electrodes through the inflation medium, and wherein a conducting wire of the second electrode is adapted for returning the RF current to the RF generator.

In another preferred embodiment, the catheter sheath is a guidewire having a distal tip section, a distal end and a proximal end. An inflatable balloon is secured to the distal tip section of the guidewire, like an over-the-wire balloon. A guiding catheter system may further comprise an additional guidewire, a guide-balloon, a soft tip section, or the like to be secured to the sheath distal end of the catheter sheath for guiding the guiding catheter toward an appropriate site of a patient. A guiding catheter system may further comprise a steering mechanism at the handle for controlling the deflection of the sheath tip section of the guiding catheter. The steering mechanism may provide a plurality of deflectable curves on the sheath tip section of the guiding catheter. A steering mechanism is well known to one who is skilled in the art.

The inflatable balloon or a guide-balloon is made of a material selected from the group consisting of polyethylene, cross-linked polyethylene, polyethylene terephthalate, silicone, polyurethane, latex, semi-permeable membrane, and nylon. The pressure for balloon inflation is about one atmosphere to about 20 atmospheres. The plurality of electrodes in this invention is made of a material selected from the group consisting of platinum, iridium, gold, silver, stainless steel, Nitinol, and an alloy of their mixtures. In the case of using an ultrasonic transducer as a heating element, the ultrasonic transducer is made of a ceramic that is coated by nickel or other suitable metal. In an optional embodiment, a guiding catheter system comprises at least one opening at the sheath tip section adapted for a biological fluid to flow and communicate between the distal end and the proximal end of the catheter sheath. A guiding catheter system further comprises a temperature sensor mounted at the close proximity of the plurality of electrodes and the guiding catheter system comprises a closed-loop temperature controller, wherein the temperature sensor is adapted for providing temperature signals to the closed-loop temperature controller for controlling the RF current delivery.

In a particular embodiment, the at least one electrode for RF applications in this invention is a cap electrode, a ring electrode, a square electrode, or an irregularly-shaped electrode secured to an inner side of the catheter shaft. The at least one electrode is preferably located close to the balloon, but outside of the balloon structure so that not to obstruct the balloon functions. When a balloon is deflated, the balloon do not compress upon the at least one electrode. The surface area of the at least one electrode is directly related to the RF energy delivery. Therefore, a rough surface may deliver more energy than a smooth surface.

In order to provide increased torsional rigidity to the catheter shaft of the guiding catheter, the shaft material preferably comprises a polymeric tube having a Durometer in the range from 30D to 90D, usually from 40D to 65D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of hepafin or anti-thrombotic substrate on the surface of the catheter shaft. It is hypothesized that the coated heparin forms a barrier, while not releasing heparin from said surface, between the blood and the catheter surface to enhance biocompatibility during electrophysiology procedures.

In an alternate embodiment, a guiding catheter comprises a catheter sheath having a sheath distal end, a sheath proximal end, and at least one lumen extending between the sheath distal end and the sheath proximal end. The at least one lumen includes an inflation lumen, the inflation lumen having a proximal end and a distal end. A handle is attached to the proximal end of the catheter sheath, wherein the handle has a cavity. The guiding catheter comprises an inflatable balloon having a balloon body and at least one balloon stem, wherein a first end of the at least one balloon stem is coupled to the balloon body while a second end of the at least one balloon stem is coupled to the inflation lumen, adapted as a passageway for an inflation medium to communicate between the inflation lumen and the balloon body. In another embodiment, a second balloon stem is included to circulate the inflation medium to further modulate the medium temperature. A plurality of electrodes is mounted inside the at least one balloon stem close to the inflation lumen, each electrode having a conducting wire. In a separate embodiment, an ultrasonic transducer may be used as the heating element for providing thermal energy to the inflation medium. The ultrasonic wave can be provided by an ultrasonic wave generator.

The system further comprises a RF current generator, wherein the RF current generator is adapted for delivering a RF current to a first electrode of the plurality of electrodes, wherein the first electrode of the plurality of electrodes is adapted for transmitting the RF current to a second electrode of the plurality of electrodes through the inflation medium, and wherein a conducting wire of the second electrode is adapted for returning the RE current to the RE generator.

A method for operating a guiding catheter system inside a heart chamber or other tissue organ, the method comprising the steps of (a) percutaneously introducing the catheter sheath through a blood vessel to the heart chamber close to an ostium of a pulmonary vein; (b) inflating the inflatable balloon; (c) intimately contacting the balloon on the ostium of a pulmonary vein; (d) applying RF current to the first electrode of the plurality of electrodes; (e) deflating the balloon; and (f withdrawing the catheter sheath from the patient.

The method and the guiding catheter of the present invention have several significant advantages over known catheters or ablation techniques. In particular, the self-guiding catheter having a uniformly heated balloon of this invention may result in a complete circular lesion that is highly desirable in the paroxysmal AFib treatment and other medical applications.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
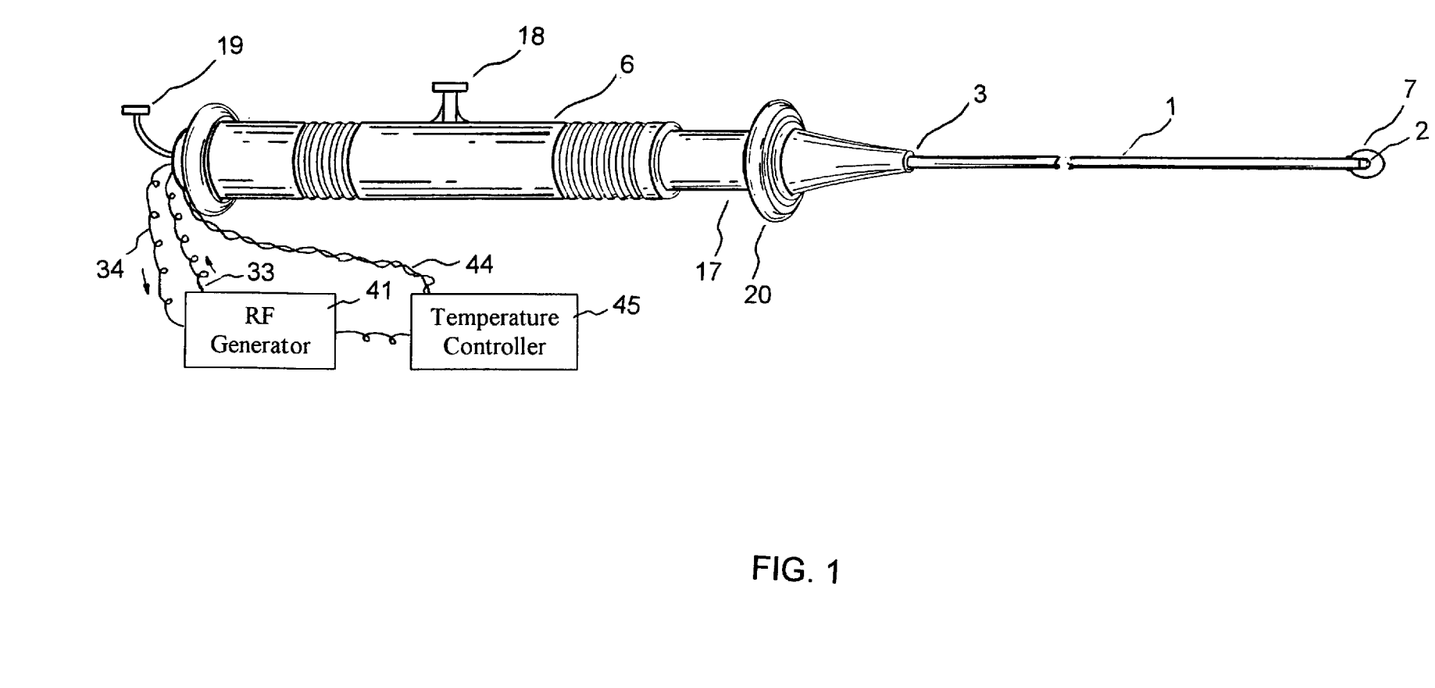
FIG. 1 is an overall view of a preferred guiding catheter system comprising a guide-balloon constructed in accordance with the principles of the present invention.

Referring to FIGS. 1 to 6, what is shown is a preferred embodiment of the guiding catheter system, comprising a guidewire 21, a guide-balloon 7, a soft tip section, or then like constructed in accordance with the principles of the present invention. FIG. 1 shows an overall view of a preferred guiding catheter system comprising a guide-balloon (also known as an inflatable balloon) at the distal end. In one preferred embodiment, a guiding catheter system comprises a catheter sheath 1 having a sheath distal end 2, a sheath proximal end 3, and at least one lumen 4 extending between the sheath distal end 2 and the sheath proximal end 3. The at least one lumen 4 includes an inflation lumen 14, 54 wherein the inflation lumen 14 has a proximal end and a distal end 15. A handle 6 is attached to the proximal end 3 of the catheter sheath 1, wherein the handle 6 has a cavity. The guiding catheter also comprises an inflatable balloon 7 having a proximal end 8 and a distal end 9) The inflatable balloon 7 may serve as the guide-balloon for the guiding catheter. The guide-balloon has at least one radiopaque marker 10 that can be identified and viewed externally of the human body. An inflation medium is used to inflate the inflatable balloon 7. The inflation medium may be selected from the group consisting of electrically conductive or semi-conductive fluids. Alternately, the inflation medium may be selected from the group consisting of electrically conductive or semi-conductive gels. In one embodiment, the electrically conductive or semi-conductive gel may contain a plurality of tiny metal particles, wherein the metal particles are adapted for providing electrical conductivity for the electrically conductive or semi-conductive gel.

In another embodiment, the guiding catheter further comprises a sheath tip section 11 that is located close to the distal end 2 of the catheter sheath. The sheath tip section 11 has a proximal end and a distal end, wherein the distal end 15 of the inflation lumen 14 opens into and is in communication with an interior 16 of the inflatable balloon 7 and wherein the proximal end 8 and/or the distal end 9 of the inflatable balloon 7 are sealed to the catheter sheath 1 at the sheath tip section 11. When a balloon is secured to the sheath distal end, only the proximal end 8 of the balloon is sealed to the catheter sheath.

Figure 2:
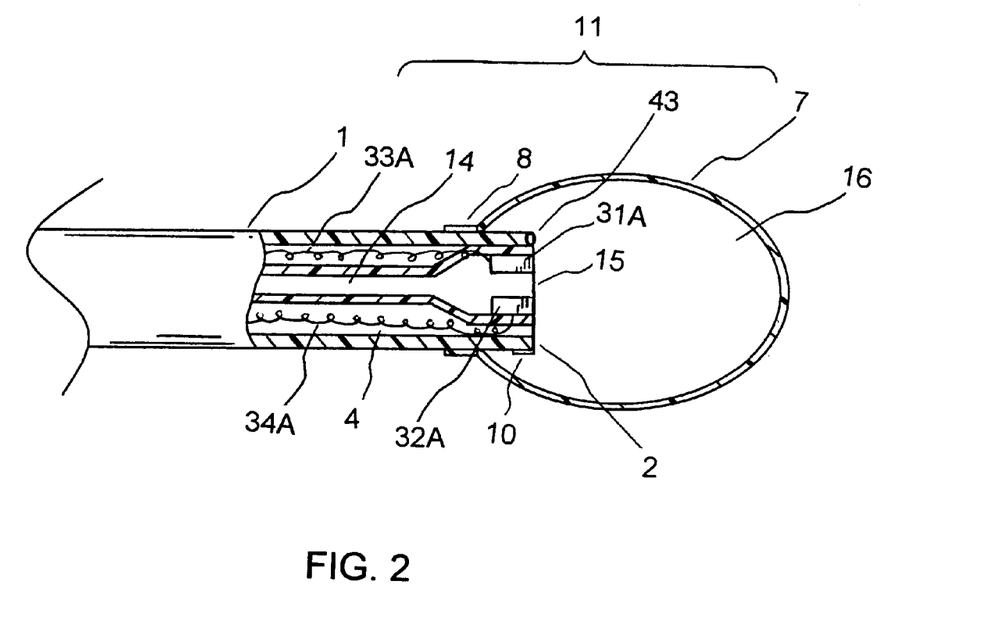
FIG. 2 is a front cross-sectional view of the distal portion of a preferred guiding catheter system having a balloon at the distal end of the catheter shaft.

FIG. 2 shows a front cross-sectional view of the distal portion of a preferred guiding catheter system having a balloon at the distal end of the catheter shaft. In a preferred embodiment, a plurality of electrodes 31A, 32A, 31B, 32B, is mounted close to the distal end 15 of the inflation lumen 14, each electrode having a conducting wire 33A, 34A, 33B, 34B. The system comprises a RF current generator 41, wherein the RF current generator is adapted for delivering a RF current to a first electrode 31 of the plurality of electrodes, wherein the first electrode 31 of the plurality of electrodes is adapted for transmitting the RE current to a second electrode 32 of the plurality of electrodes through the inflation medium 42, and wherein a conducting wire 34 of the second electrode 32 is adapted for returning the RF current to the RF generator 41.

Figure 3:
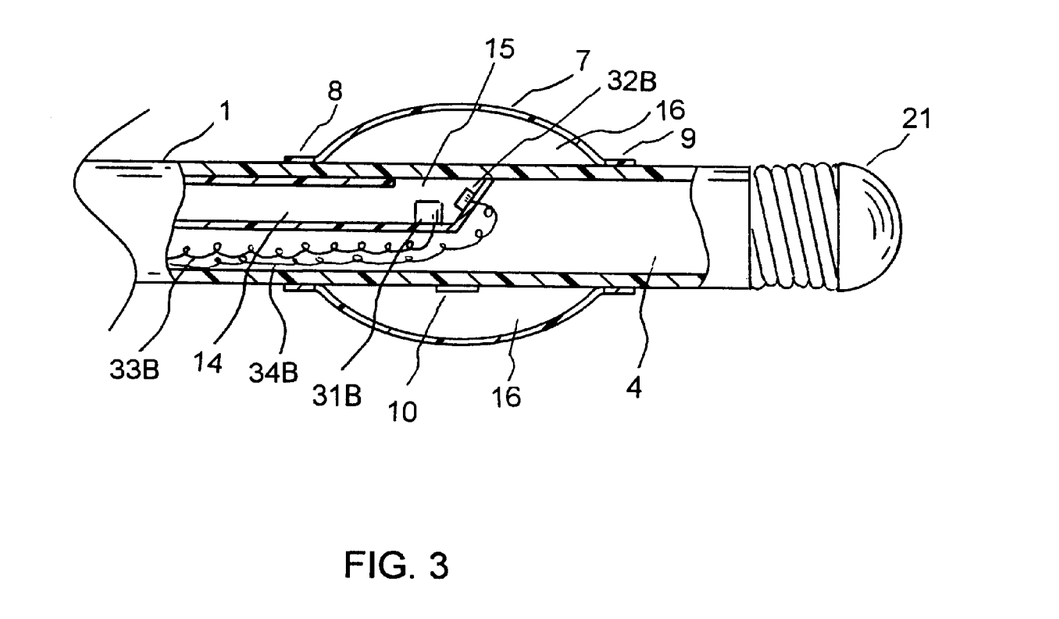
FIG. 3 is a front cross-sectional view of the distal tip portion of a preferred guiding catheter system having a balloon at the sheath distal section.

FIG. 3 shows a front cross-sectional view of the distal tip portion of a preferred guiding catheter system having a balloon at the sheath distal section. A guiding catheter system may further comprises a guidewire 21, a guide-balloon 7, or the like to be secured to the sheath distal end of the catheter sheath 11 for guiding the guiding catheter toward an appropriate site of a patient. A guiding catheter system may further comprise a steering mechanism 17 at the handle 6 for controlling the deflection of the sheath tip section 11 of the guiding catheter. In one embodiment, by pushing the front plunger 20 of the handle 6, the sheath tip section 11 of the guiding catheter deflects to one direction. By pulling the front plunger 20, the sheath tip section returns to its neutral position. In another embodiment, the steering mechanism 17 at the handle 6 comprises means for providing a plurality of deflectable curves on the distal tip section of the guiding catheter. A steering mechanism is well known to one who is skilled in the art.

The inflation fluid or gel is introduced from the fluid inlet port 18 through an inflation lumen 14 to the lumen distal end 15 of the inflation lumen, whereby the inflation fluid or gel is introduced into an interior 16 of the balloon 7. A separate port 19 is used for inserting an inner catheter to be inserted or guided inside the guiding catheter. The inner catheter can be used for fluid infusion, mapping, or ablation purposes.

Figure 4:
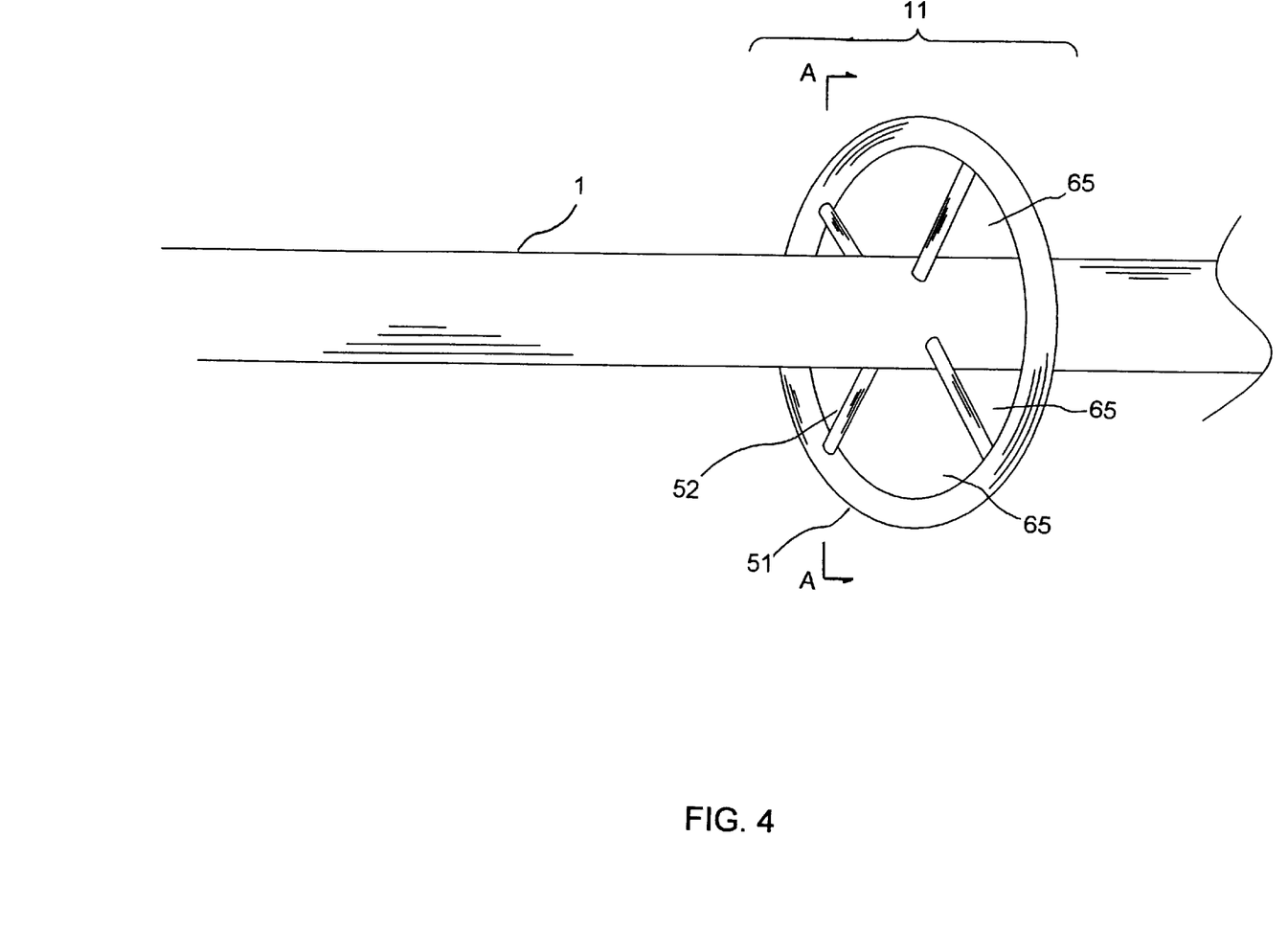
FIG. 4 is a front cross-sectional view of the distal tip portion of an alternate guiding catheter system having a balloon body and balloon stems at the sheath distal section.
Figure 5:
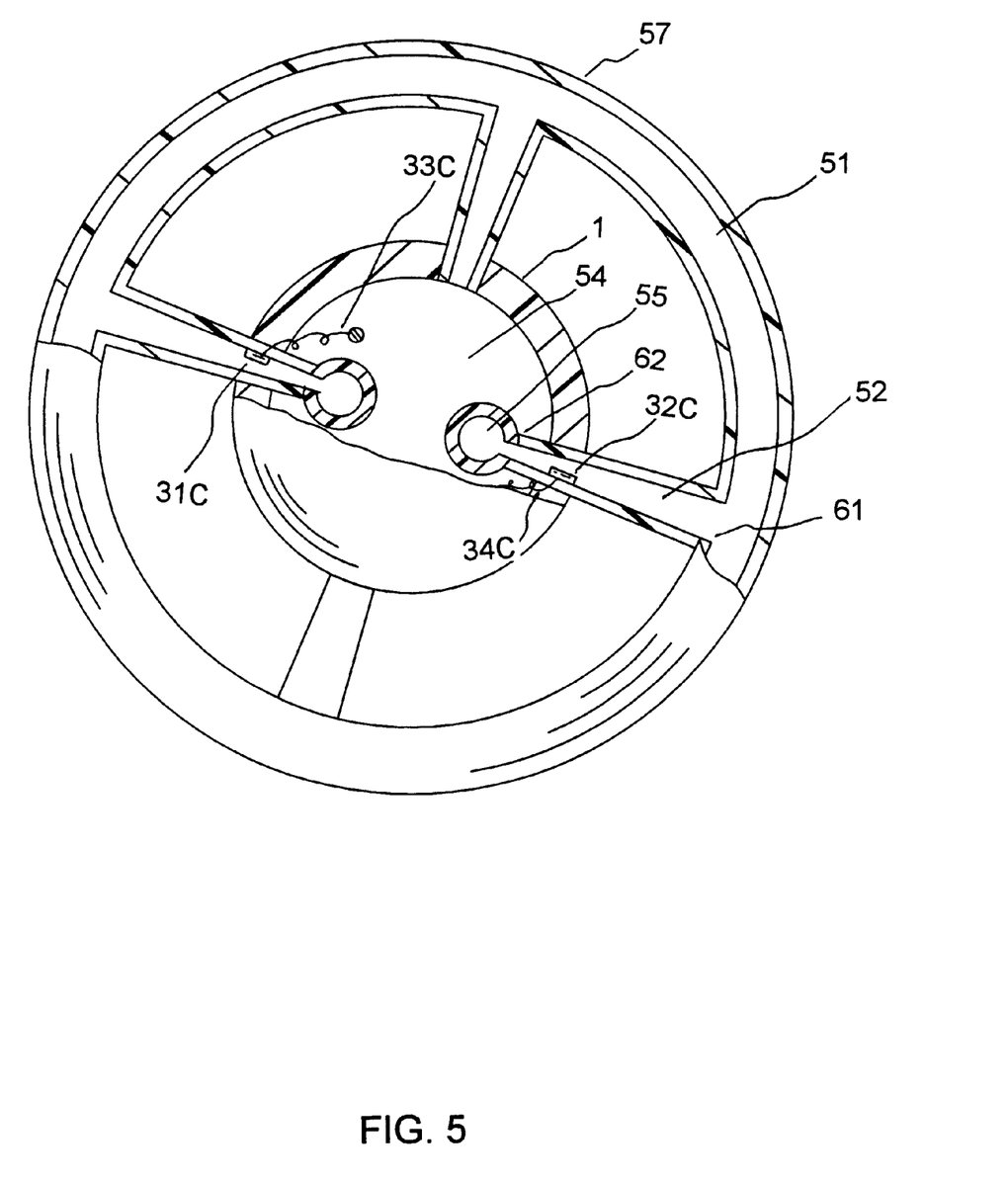
FIG. 5 is a side cross-sectional view, section A—A of FIG. 4, of the balloon means having a balloon body and balloon stems at the sheath distal section.

FIG. 4 shows a front cross-sectional view of the distal tip portion of an alternate guiding catheter system having a balloon body 51 and at least one balloon stem 52 at the sheath distal section 11. FIG. 5 shows a side cross-sectional view, section A—A of FI(3. 4, of the balloon means having a balloon body 51 and at least one balloon stem 52 at the sheath distal section 11.

In an alternate embodiment as shown in FIGS. 4 and 5, the guiding catheter system comprises a catheter sheath 1 having a sheath distal end, a sheath proximal end, and at least one lumen 54 extending between the sheath distal end and the sheath proximal end. The at least one lumen includes an inflation lumen 55, the inflation lumen 55 having a proximal end and a distal end. A handle 6 is attached to the proximal end of the catheter sheath 1, wherein the handle has a cavity. The catheter system comprises an inflatable balloon 57 having a balloon body 51 and at least one balloon stem 52, wherein a first end 61 of the at least one balloon stem 52 is coupled to the balloon body 51 while a second end 62 of the at least one balloon stem 52 is coupled to the inflation lumen 55, adapted as a passageway for an inflation medium to communicate between the inflation lumen 55 and balloon body 51.

A plurality of electrodes 31C, 32C is mounted inside the at least one balloon stem 52 close to the inflation lumen 55, each electrode having a conducting wire 33C, 34C. The catheter system further comprises a RF current generator 41, wherein the RF current generator is adapted for delivering a RF current to a first electrode 31C of the plurality of electrodes, wherein the first electrode 31C of the plurality of electrodes is adapted for transmitting the RF current to a second electrode 32C of the plurality of electrodes through the inflation medium 42, and wherein a conducting wire 34C of the second electrode 32C is adapted for returning the RF current to the RF generator 41.

The inflatable balloon 57 may be made of a material selected from the group consisting of polyethylene, cross-linked polyethylene, polyethylene terephthalate, silicone, polyurethane, latex, semi-permeable membrane, and nylon. The inflation medium may be selected from the group consisting of electrically conductive or semi-conductive fluids. Alternately, the inflation medium may be selected from the group consisting of electrically conductive or semi-conductive gels, wherein the electrically conductive or semi-conductive gel may contain a plurality of metal particles and the metal particles are adapted for providing electrical conductivity for the electrically conductive or semi-conductive gel.

The guiding catheter system further comprises at least one opening 65 bordered among the balloon body 51, the balloon stem 52, and the catheter sheath 1, adapted for a biological fluid to flow between the distal end and the proximal end of the catheter sheath 1 when the guiding catheter is deployed inside a tubular organ.

Figure 6:
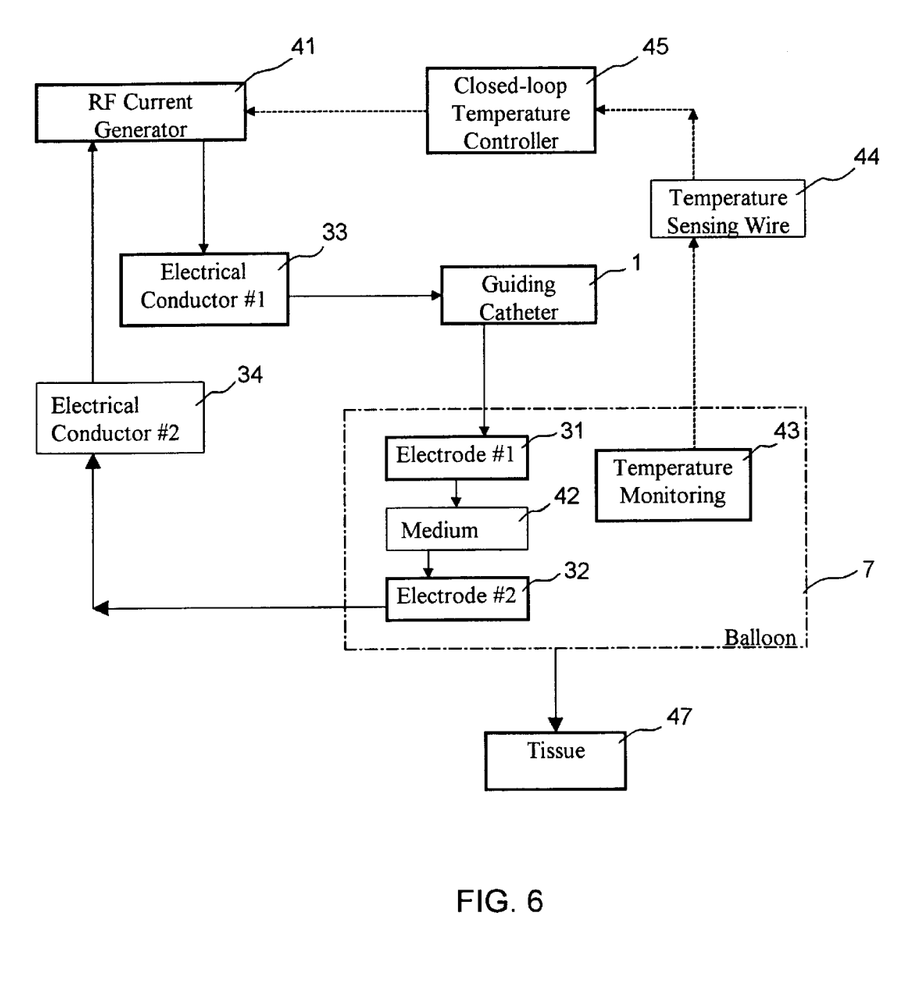
FIG. 6 is a schematic diagram of a RF treatment method in relation to the tissues through a heated balloon means in a patient.

A temperature sensor 43, either a thermocouple means or a thermister means, is constructed at the proximity of one electrode to measure the temperature of the inflation medium 42 inside a balloon when RF energy is delivered between a first electrode 31 and a second electrode 32 through a conductive or semi-conductive fluid/gel medium inside a balloon 7, This is illustrated in FIG. 6. The temperature sensing wire 44 from the thermocouple or thermister is connected to one of the contact pins of the connector on the handle 6 and externally connected to a transducer and to a temperature controller 45. The temperature reading is thereafter relayed to a closed-loop control mechanism 45 to adjust the RF current output. The RF energy delivered is thus controlled by the temperature sensor reading or by a pre-programmed control mechanism.

The RF current can be applied to the first electrode continuously, intermittently or controlled by the temperature controller 45. The heat generated by the inflation medium 42 at the electrode sites is dispersed within the inflation medium and indirectly heat the balloon itself. The balloon surface would attain a relatively uniform elevated temperature, wherein the elevated temperature is used to ablation the tissue 47 at a pre-determined therapeutic temperature.

From the foregoing, it should now be appreciated that an improved guiding catheter system comprising a plurality of electrodes inside an inflatable balloon filled with conductive and/or semi-conductive inflation medium has been disclosed for ablation procedures, including endocardial, epicardial, or body tissue ablations. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A guiding catheter system comprising:

a catheter sheath having a sheath distal end, a sheath proximal end, and at least one lumen extending, between the sheath distal end and the sheath proximal end, wherein the at least one lumen includes an inflation lumen, the inflation lumen having a proximal end and a distal end;

a handle attached to the proximal end of the catheter sheath, wherein the handle has a cavity;

an inflatable balloon having a proximal end and a distal end, wherein the inflatable balloon is made of a material selected from the group consisting of polyethylene, cross-linked polyethylene, polyethylene terephthalate, silicone, polyurethane, latex, semi-permeable membrane, and nylon;

an inflation medium, wherein the inflation medium is used to inflate the inflatable balloon, the inflation medium being selected from the group consisting of electrically semi-conductive fluids and electrically semi-conductive gels, wherein the electrically semi-conductive gel contains a plurality of metal particles and the metal particles are adapted for providing electrical conductivity for the electrically semi-conductive gel;

a sheath tip section located close to the distal end of the catheter sheath having a proximal end and a distal end, wherein the distal end of the inflation lumen opens into and is in communication with an interior of the inflatable balloon and wherein the distal end and the proximal end of the inflatable balloon are sealed to the catheter sheath at the sheath tip section;

a plurality of electrodes mounted close to the distal end of the inflation lumen, each electrode having a conducting wire; and a RF current generator, wherein the RF current generator is adapted for delivering a RF current to a first electrode of the plurality of electrodes, wherein the first electrode of the plurality of electrodes is adapted for transmitting the RF current to a second electrode of the plurality of electrodes through the inflation medium, and wherein a conducting wire of the second electrode is adapted for returning the RF current to the RF general.

2. A guiding catheter system comprising:

a catheter sheath having a sheath distal end, a sheath proximal end, and at least one lumen extending between the sheath distal end and the sheath proximal end, wherein the at least one lumen includes an inflation lumen, the inflation lumen having a proximal end and a distal end;

a handle attached to the proximal end of the catheter sheath, wherein the handle has a cavity;

an inflatable balloon having a balloon body and at least one balloon stem, wherein a first end of the at least one balloon stem is coupled to the balloon body while a second end of the at least one balloon stem is coupled to the inflation lumen, adapted as a passageway for an inflation medium to communicate between the inflation lumen and the balloon body;

a plurality of electrodes mounted inside the at least one balloon stem close to the inflation lumen, each electrode having a conducting wire; and a RF current generator, wherein the RF current generator is adapted for delivering a RF current to a first electrode of the plurality of electrodes, wherein the first electrode of the plurality of electrodes is adapted for transmitting the RF current to a second electrode of the plurality of electrodes through the inflation medium, and wherein a conducting wire of the second electrode is adapted for returning the RF current to the RF generator.

3. A guiding catheter system as in claim 2 further comprising at least one opening at the sheath tip section adapted for a biological fluid to flow between the distal end and the proximal end of the catheter sheath.

4. A guiding catheter system of claim 2, wherein the inflatable balloon is made of a material selected from the group consisting of polyethylene, cross-linked polyethylene, polyethylene terephthalate, silicone, polyurethane, latex, semi-permeable membrane, and nylon.

5. A guiding catheter system of claim 2, wherein the inflation medium is selected from the group consisting of electrically semi-conductive fluids.

6. A guiding catheter system of claim 2, wherein the inflation medium is selected from the group consisting of electrically semi-conductive gels.

7. A guiding catheter system of claim 6, wherein the electrically semi-conductive gel contains a plurality of metal particles and the metal particles are adapted for providing electrical conductivity for the electrically semi-conductive gel.

8. A guiding catheter system of claim 2, wherein the plurality of electrodes is made of a material selected from the group consisting of platinum, iridium, gold, silver, stainless steel, Nitinol, and an alloy of their mixtures.

9. A guiding catheter system as in claim 2 further comprising at least one opening bordered among the balloon body, the at least one balloon stem, and the catheter sheath, adapted for a biological fluid to flow between the distal end and the proximal end of the catheter sheath.

10. A method for operating a guiding catheter system within a heart chamber or a tubular organ, the guiding catheter system comprising a catheter sheath having a sheath distal end, a sheath proximal end, and at least one lumen extending between the sheath distal end and the sheath proximal end, wherein the at least one lumen includes an inflation lumen, the inflation lumen having a proximal end and a distal end; a handle attached to the proximal end of the catheter sheath, wherein the handle has a cavity; an inflatable balloon having a balloon body and at least one balloon stem, wherein a first end of the at least one balloon stem is coupled to the balloon body while a second end of the at least one balloon stem is coupled to the inflation lumen, adapted as a passageway for an inflation medium to communicate between the inflation lumen and the balloon body;

a plurality of electrodes mounted inside the at least one balloon stem close to the inflation lumen, each electrode having a conducting wire; and a RF current generator, wherein the RF current generator is adapted for delivering a RF current to a first electrode of the plurality of electrodes, wherein the first electrode of the plurality of electrodes is adapted for transmitting the RF current to a second electrode of the plurality of electrodes through the inflation medium, and wherein a conducting wire of the second electrode is adapted for returning the RF current to the RF generator;

the method comprising the steps of:
(a) percutaneously introducing the catheter sheath through a blood vessel to the heart chamber close to an ostium of a pulmonary vein;
(b) inflating the inflatable balloon;
(c) intimately contacting the balloon on an ostium of a pulmonary vein;
(d) applying RF current to the first electrode of the plurality of electrodes;
(e) deflating the balloon; and
(f) withdrawing the catheter sheath from the patient.

* * * * *